(12) United States Patent
Mitchell

(10) Patent No.: US 6,526,320 B2
(45) Date of Patent: Feb. 25, 2003

(54) APPARATUS FOR THERMAL TREATMENT OF TISSUE

(75) Inventor: James Mitchell, Ayer, MA (US)

(73) Assignee: United States Surgical Corporation, Norwalk, CT (US)

( * ) Notice: Subject to any disclaimer, the term of this patent is extended or adjusted under 35 U.S.C. 154(b) by 79 days.

(21) Appl. No.: 09/859,140

(22) Filed: May 16, 2001

(65) Prior Publication Data

US 2002/0002393 A1 Jan. 3, 2002

Related U.S. Application Data

(63) Continuation of application No. PCT/US99/27133, filed on Nov. 16, 1999.
(60) Provisional application No. 60/108,596, filed on Nov. 16, 1998.

(51) Int. Cl.$^7$ .................................................. A61F 2/00
(52) U.S. Cl. ........................ 607/101; 606/46; 606/41
(58) Field of Search ......................... 606/41, 45, 46, 606/47, 48, 49, 50; 607/96, 98, 99, 101, 102

(56) References Cited

U.S. PATENT DOCUMENTS

| 4,411,266 A | 10/1983 | Cosman |
| 4,565,200 A | 1/1986 | Cosman |
| 4,907,589 A | 3/1990 | Cosman |
| 5,348,554 A | 9/1994 | Imran et al. |
| 5,366,490 A | 11/1994 | Edwards et al. |
| 5,370,675 A | 12/1994 | Edwards et al. |
| 5,385,544 A | 1/1995 | Edwards et al. |
| 5,389,073 A | 2/1995 | Imran |
| 5,409,453 A | 4/1995 | Lundquist et al. |
| 5,421,819 A | 6/1995 | Edwards et al. |
| 5,433,749 A | 7/1995 | Clifford et al. |
| 5,435,805 A | 7/1995 | Edwards et al. |
| 5,484,400 A | 1/1996 | Edwards et al. |
| 5,520,684 A | 5/1996 | Imran |
| 5,533,967 A | 7/1996 | Imran |
| 5,542,916 A | 8/1996 | Hirsch et al. |
| 5,545,161 A | 8/1996 | Imran |
| 5,562,703 A * | 10/1996 | Desai .......................... 604/33 |
| 5,667,488 A * | 9/1997 | Lundquist et al. ............ 604/22 |
| 5,957,922 A | 9/1999 | Imran |
| 5,993,447 A | 11/1999 | Blewett et al. |
| 5,995,875 A * | 11/1999 | Blewett et al. ............... 606/41 |
| 6,045,549 A * | 4/2000 | Smethers et al. ............. 604/22 |
| 6,302,903 B1 | 10/2001 | Mulier et al. |
| 6,356,790 B1 | 3/2002 | Maguire et al. |

* cited by examiner

Primary Examiner—Roy D. Gibson

(57) ABSTRACT

An apparatus for thermal treatment of tissue, includes an outer member having a frame dimensioned for engagement with the hand of a surgeon and an elongated portion connected to the frame and extending distally therefrom. The elongated portion defines a longitudinal axis and has an axial opening. An electromagnetic probe assembly is releasably mounted to the outer member. The electromagnetic probe assembly includes a handle and an electromagnetic probe connected to the handle. The electromagnetic probe is at least partially positionable within the axial opening of the elongated portion and is adapted for reciprocal longitudinal movement therewithin between a non-deployed position and a deployed positions. A manually operable release member releasably mounts the electromagnetic probe assembly to the outer member. The release member is dimensioned and positioned for manual manipulation to move between a first position engaging the electromagnetic probe assembly and preventing release thereof from the outer member, and a second position releasing the electromagnetic probe assembly to thereby facilitate assembly and disassembly of the electromagnetic probe assembly with respect to the outer member.

18 Claims, 14 Drawing Sheets

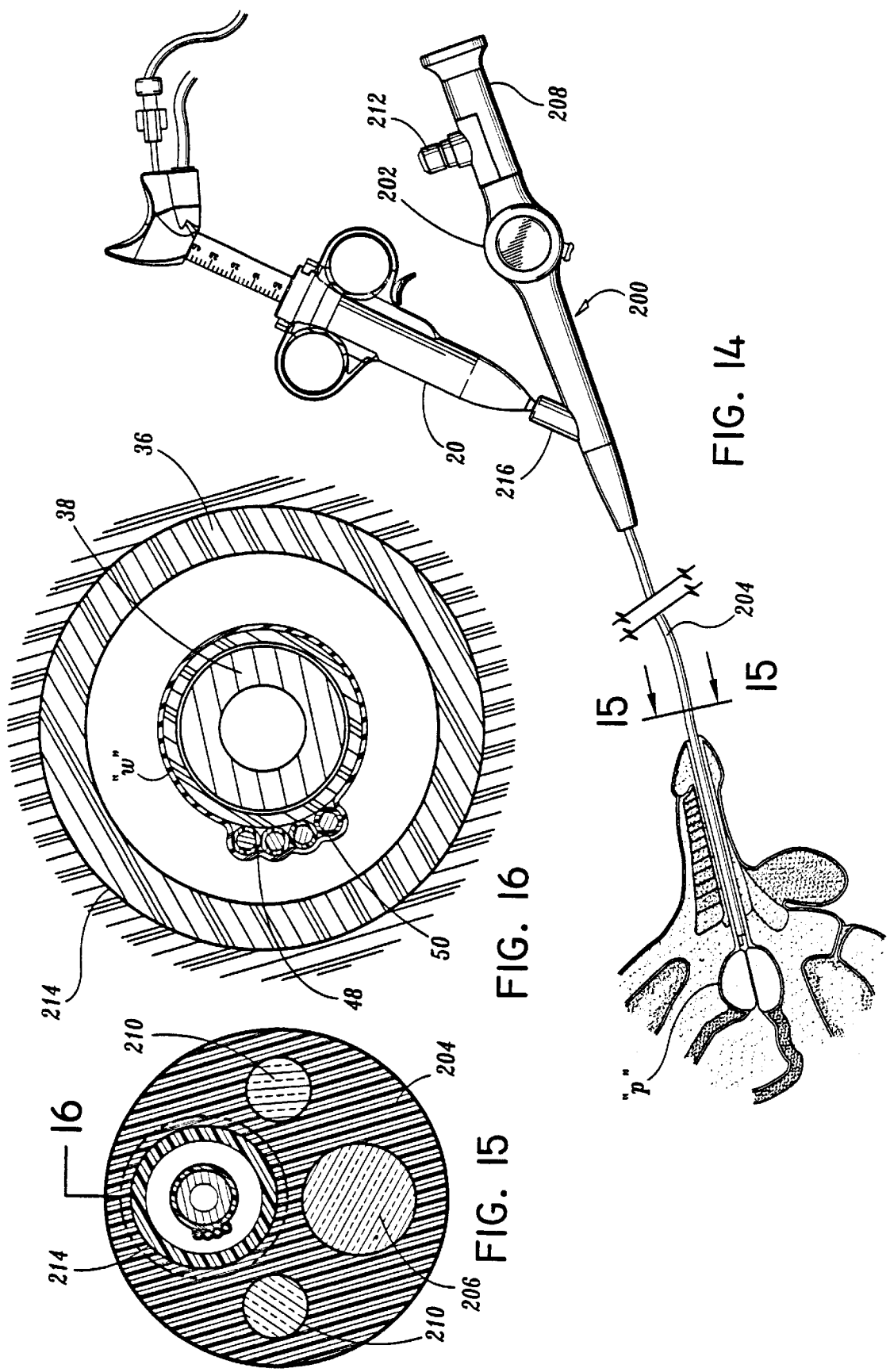

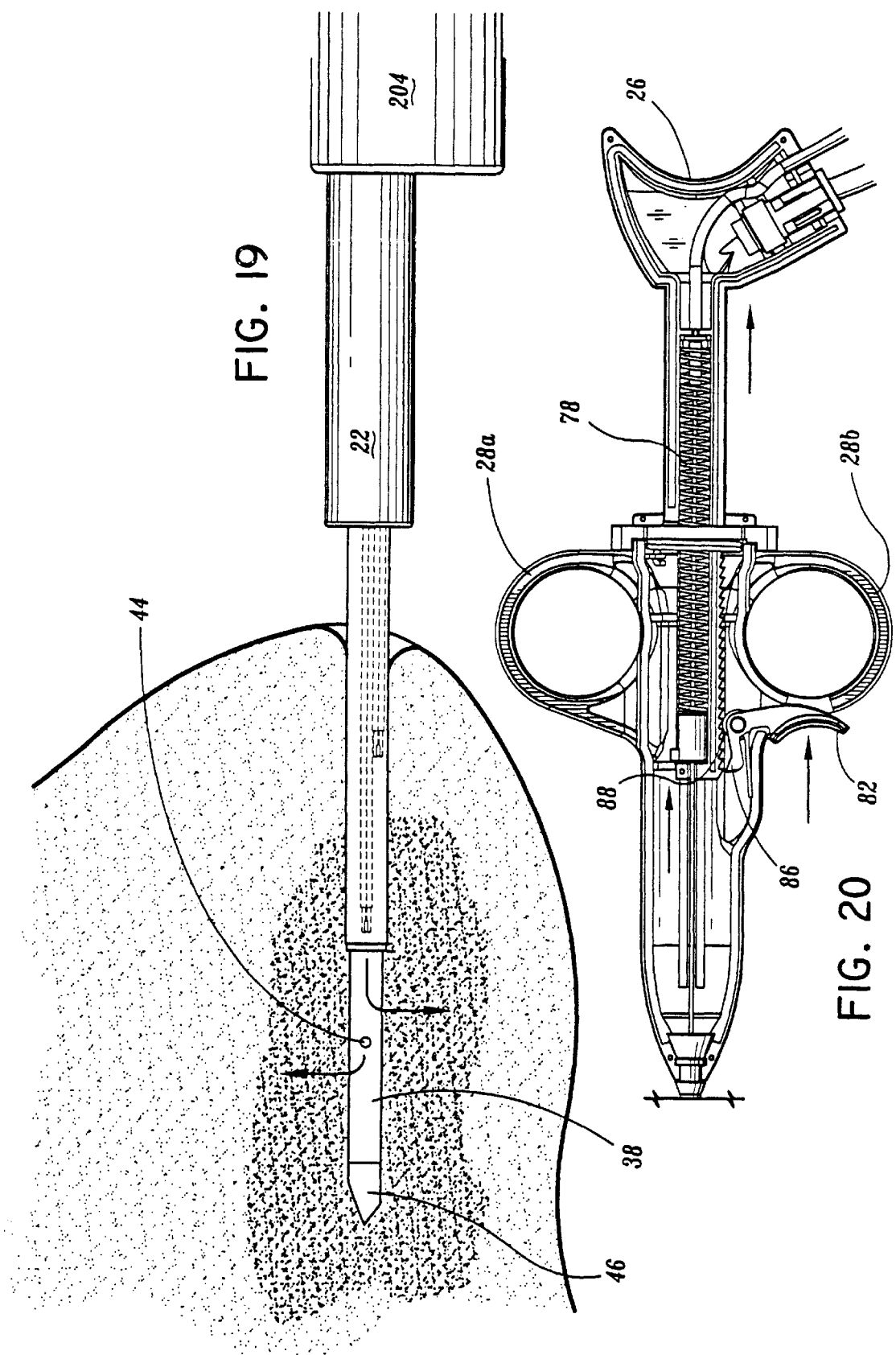

APPARATUS FOR THERMAL TREATMENT OF TISSUE

This application claims the benefit of Provisional Application No. 60/108,596 filed Nov. 16, 1998, and is a continuation of PCT/US99/27133 filed Nov. 16, 1999.

BACKGROUND

1. Technical Field

The present disclosure relates generally to a method and apparatus for thermal treatment of tissue and, more particularly, to an apparatus to be used with a conventional endoscope to provide the endoscope with thermal treatment capabilities. The apparatus is particularly contemplated for use with a cystoscope or a urethroscope for hyperthermia treatment of prostatic tissue.

2. Background of the Related Art

Benign prostate hyperplasia (BPH) or hyperplasia affects over one out of every two males over the age of fifty. BPH is the non-cancerous enlargement of the prostate gland and is characterized generally by a constriction of the urethra by the prostate gland. An array of symptoms are associated with BPH including frequent urination, complications in urinary flow and associated pain.

Generally there are two primary methods for treating BPH, namely, drug therapy and surgical intervention. Drug therapy incorporates the use of one or more drugs such as Proscar™ and Hydrin™ to either reduce the size of the prostate or to relax the urethral muscles thereby facilitating the normal functioning of the urinary system. Known drug therapies, however, are limited in their effectiveness and present many drug side effect concerns.

Surgical methods for treating BPH include transurethral resection of the prostate (TURP), transurethral incision of the prostate (TUIP), visual laser assisted prostatectomy (VLAP), balloon dilation and stenting. TURP is the most common method employed for BPH treatment today and involves the insertion of an electrosurgical cutting instrument through the urethral passage. The cutting elements of the instrument are positioned adjacent the prostate gland, and the instrument is energized such that the cutting elements selectively cauterize and resect tissue from the core of the prostate. The TURP procedure, however, has many side effects including bleeding, electrograde ejaculation, impotence, incontinence, edema and a prolonged recovery period for the patient. An example of an electrosurgical cutting instrument utilized in conjunction with a TURP procedure is disclosed in U.S. Pat. No. 5,192,280.

Transurethral incision of the prostate (TUIP) involves the use of an electrocautery device which is passed through the urethra. The device is employed to make multiple incisions in the prostate, thereby permitting the prostate to be displaced from the urethra wall to create an opening for urine flow. Success with the TUIP procedure is generally limited providing only temporary reprocedure in the future.

Visual laser assisted prostatectomy (VLAP) includes insertion of a laser catheter through the urethra and directing laser energy laterally through the catheter sleeve at the urethral wall and the prostatic tissue. The laser energy causes the tissue to coagulate. The coagulated tissue eventually necrosis from lack of blood flow and is naturally removed from the body. Drawbacks of VLAP include increased recovery time, acute pain and irritation, and undesired burning of the urethral wall. Examples of methods and apparatuses utilized in VLAP treatment of BPH are disclosed in U.S. Pat. No. 5,242,438 to Saadatmanesh et al. and U.S. Pat. No. 5,322,507 to Costello.

Balloon dilation and stenting procedures for BPH involve expanding and stretching the enlarged prostate with a balloon catheter to relieve pressure off the constricted urethra while stenting incorporates the insertion of tiny wire-mesh coils which expand into a scaffold to hold the urethra open. Balloon dilation and stenting, however, are only temporary procedures typically requiring follow up within a year period. In addition, stenting presents complications of stent migration and consequent irritation.

Transurethral microwave therapy (TUMT) and high intensity focused ultrasound (HIFU) have been developed for the treatment of BPH. In accordance with a TUMT procedure, a foley-type urethral catheter having a microwave emitting antenna at a probe end is inserted into the urethral passage for a period of time sufficient to treat the tissue by microwave radiation. Intraurethral applicators of this type are described in U.S. Pat. Nos. 4,967,765, 5,234,004 and 5,326,343. The drawbacks of TUMT include the inability to focus the heat energy in the prostatic area and the inability to achieve high temperatures uniformly within the prostate.

High intensity focused ultrasound (HIFU) includes directing high intensity ultrasound waves at the prostate tissue to create heat in a precise area to coagulate and necrose tissue. A transurethral probe is utilized to create the ultrasound beams for both imaging and ablation of the prostatic tissue. Disadvantages of this procedure include the inability to directly focus the ultrasound energy at the prostatic tissue.

A more recent form of treatment for BPH involves thermally treating prostatic tissue with radio frequency electromagnetic energy. For example, one current technique, known as transurethral needle ablation (TUNA™), involves the transurethral application of a medical instrument having a built-in RF needle electrode system. The TUNA™ instrument is inserted into the urethra and advanced to a position adjacent the prostate. Thereafter, the RF needles are advanced to penetrate the urethral wall and access the prostatic tissue. The RF system is activated whereby a RF current is transmitted through each electrode to pass through the tissue to a grounding pad thereby forming a necrotic legion which is eventually absorbed by the body. Apparatuses and methods for treating BPH via the TUNAS technique are disclosed in U.S. Pat. Nos. 5,366,490; 5,370,675; 5,385,544; 5,409,453; 5,421,819; 5,435,805; 5,470,308; 5,470,309; 5,484,400; and 5,486,161.

Although the TUNA technique is encouraging in thermal ablation procedures, particularly, in the thermal treatment of BPH, there are several disadvantages inherent to these instruments which detract from their usefulness. In particular, the TUNA instruments are generally complex typically incorporating built in optical systems, aspiration systems, etc. . . . In addition, the TUNA instruments incorporate a complex mechanism for advancing and retracting the RF needles within the tissue and relative to the insulating sleeves. As a result, the instruments are relatively expensive to manufacture thereby precluding disposability of the instrument after a minimal number of uses. Moreover, conventional TUNA instruments are generally enlarged by virtue of the various systems incorporated within the instrument, thus, increasing patient trauma and discomfort during use.

Accordingly, the present disclosure is directed to an apparatus for the RF thermal treatment of prostatic tissue. This apparatus is intended for use in conjunction with a conventional cystoscope and incorporates an RF system and associated mechanism that is at least partially positionable within the working channel of the cystoscope. The apparatus, by use in conjunction with a conventional cystoscope, makes use of the existing systems, e.g., optical and illumination, of in a less complex and less expensive RF thermal treatment device. Furthermore, the apparatus may be used in cystoscopes as small as 5 mm in diameter thereby providing a less invasive system for transurethral ablation as compared to the TUNA instruments and technique. In addition, the apparatus incorporates a novel assembly mechanism which permits the user to selectively couple a variety of RF electrode units having different energy transmitting capabilities to the apparatus to accommodate desired operative parameters.

SUMMARY

An apparatus for thermal treatment of tissue, includes an outer member having a frame dimensioned for engagement with the hand of a surgeon and an elongated portion connected to the frame and extending distally therefrom. The elongated portion defines a longitudinal axis and has an axial opening. An electromagnetic probe assembly is releasably mounted to the outer member. The electromagnetic probe assembly includes a handle and an electromagnetic probe connected to the handle. The electromagnetic probe is at least partially positionable within the axial opening of the elongated portion and is adapted for reciprocal longitudinal movement therewithin between a non-deployed position and a deployed position. A manually operable release member releasably mounts the electromagnetic probe assembly to the outer member. The release member is dimensioned and positioned for manual manipulation to move between a first position engaging the electromagnetic probe assembly and preventing release thereof from the outer member, and a second position releasing the electromagnetic probe assembly to thereby facilitate assembly and disassembly of the electromagnetic probe assembly with respect to the outer member. The release member is preferably mounted to the frame of the outer member and is rotatable about the longitudinal axis to move between the first and second positions thereof.

The handle of the electromagnetic probe assembly includes a handle extension which is received within the central opening of the release member. The release member is preferably normally biased to the first position thereof.

The release member may define an inner cam surface adjacent the opening. Similarly, the handle extension of the handle defines a corresponding outer cam surface. The outer cam surface cooperates with the inner cam surface upon advancement of the handle extension within the release member to move the release member to the second position thereof.

The handle extension may define an outer rail. The outer rail defines the outer cam surface at its distal end and defines an abutment surface at its proximal end. The abutment surface is dimensioned and configured to engage the release member to prevent removal of the electromagnetic probe assembly from the outer member when the release member is in the first position thereof and the electromagnetic probe is assembled with respect to the outer member. The frame of the outer member includes at least one longitudinal recess dimensioned for reception of the one outer rail to prevent rotational movement of the electromagnetic probe assembly relative to the outer member.

The apparatus may include a ratchet and associated pawl mechanism for permitting controlled incremental movement of the electromagnetic probe assembly toward the deployed position while preventing movement of the electromagnetic probe assembly toward its non-deployed position. A manually engageable release trigger depends from the frame. The release trigger is movable to disengage the ratchet and associated pawl mechanism thereby permitting movement of the electromagnetic probe toward the non-deployed position.

In a preferred embodiment, the electromagnetic probe includes a radio frequency electrode. The electromagnetic probe may define an axial channel for passage of fluids, and at least one opening extends through an outer wall of the probe in fluid communication with the axial channel to permit exit of the fluids therefrom. A source of fluid may be in communication with the axial channel of the electromagnetic probe. The source of fluid may include one of an irrigant fluid or a conductive fluid.

BRIEF DESCRIPTION OF THE DRAWINGS

Preferred embodiments of the disclosure are described herein with respect to the drawings wherein:

FIG. 6A is an enlarged cross-sectional view of the elongated portion in the initial unactuated position of the instrument;

FIG. 14 is a view illustrating a cystoscope inserted within the urethral passage of the patient and having the electrosurgical instrument mounted within a working channel thereof;

FIG. 15 is a cross-sectional view taken along the lines 15—15 of FIG. 14 illustrating the electrosurgical instrument inserted within the working channel of the cystoscope and the components of the cystoscope;

FIG. 16 is an enlarged view of the electrosurgical instrument inserted within the cystoscope;

FIG. 19 is an enlarged view illustrating the electromagnetic probe positioned within the prostrate and ejecting an irrigant;

FIG. 20 is a cross-sectional view of the handle illustrating release of the release trigger and movement of the actuator to the initial unadvanced position;

DETAILED DESCRIPTION OF THE PREFERRED EMBODIMENTS

The apparatus of the present disclosure is intended to deliver electromagnetic energy to tissue for thermal treatment of the tissue including tissue ablation, tissue vaporization and/or tissue coagulation. The apparatus has particular application in the treatment of benign prostate hyperplasia (BPH) with electromagnetic radio frequency (RF) energy, however, it is to be appreciated that the apparatus is not limited to such application. For example, the apparatus is not limited to the treatment of BPH, but, may be used in other surgical procedures such as cardiac ablation, cancer treatment, etc. . . . Moreover, the apparatus may be used in any minimally invasive procedure where thermal treatment of tissue is desired and access to the tissue is limited.

The apparatus is particularly intended to be used in conjunction with an endoscope such as a cystoscope, fiber scope, laparoscope, urethroscope, etc . . . to provide the scope with thermal treatment capabilities. More specifically, in treatment of BPH, the apparatus may be insertable within the working channel of a cystoscope, which is positioned in the urethra to access the prostatic gland, to thermally treat the gland to relieve the symptoms of BPH.

Figure 1:
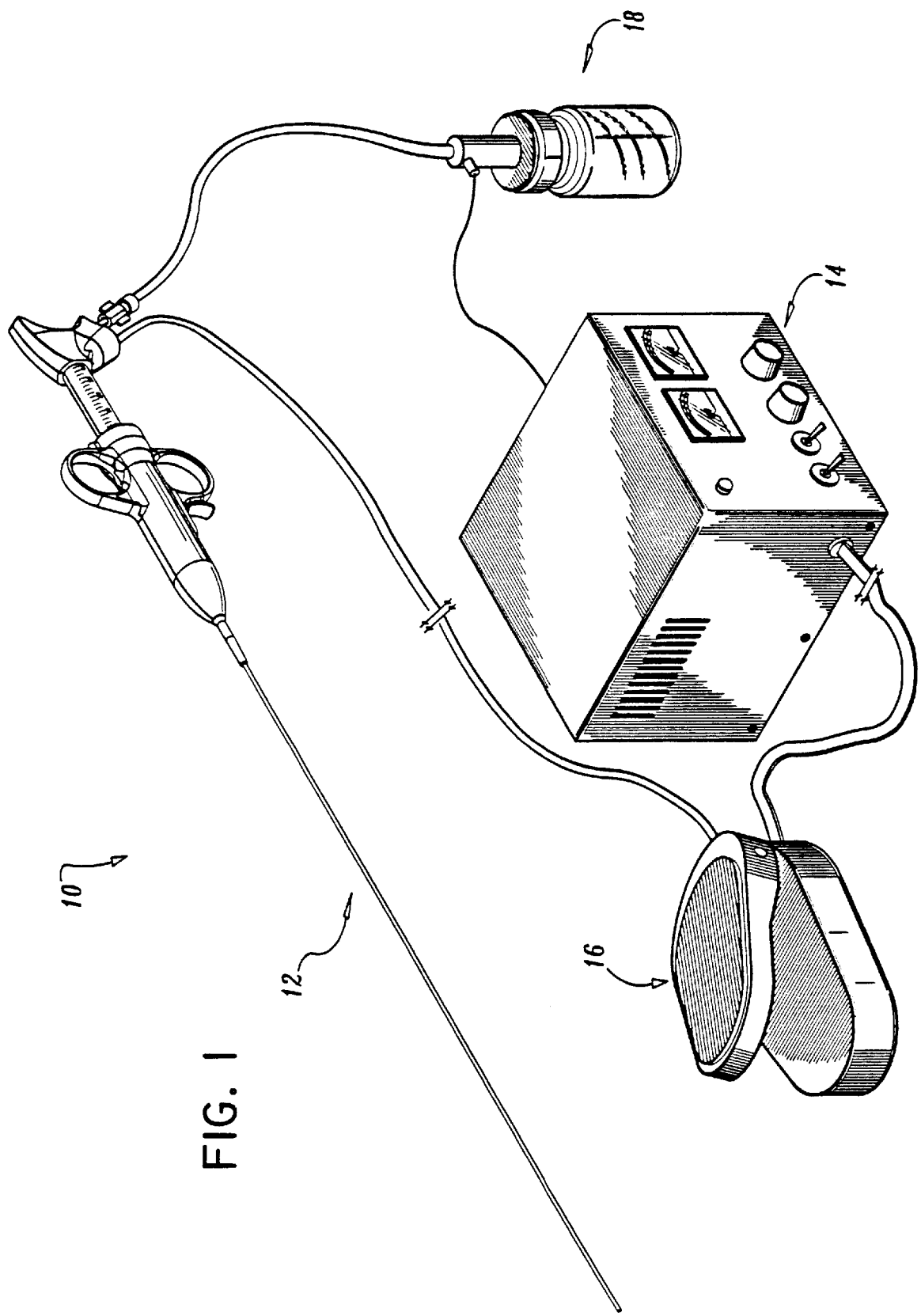
FIG. 1 is a perspective view of the thermal treatment apparatus in accordance with the principles of the present disclosure, illustrating the electrosurgical instrument, power source and foot pedal for operating the instrument.

Referring now to FIG. 1, there is illustrated the apparatus for thermal treatment of tissue in accordance with the principles of the present disclosure. Apparatus 10 includes electrosurgical instrument 12, power source 14 for supplying electromagnetic energy to the instrument 12 and foot pedal 16 for activating/deactivating the instrument 12. Apparatus 10 may further include a source of irrigant 18 which is to be supplied to the operative area. Such irrigants include water, normal saline, contrast media and the like. Alternatively, the source may include a conductive fluid such as any physiologically-compatible liquid, solution, slurry, gel, isotonic solution to facilitate the transfer of heat or energy at the operative site.

Power source 14 may be any suitable power generator capable of supplying radiofrequency energy in the frequency range of about 300 kHz–about 800 kHz. One suitable power generator is disclosed in application Ser. No. 08/948,990, filed Oct. 10, 1997, the contents of which are incorporated herein by reference.

Figure 2:
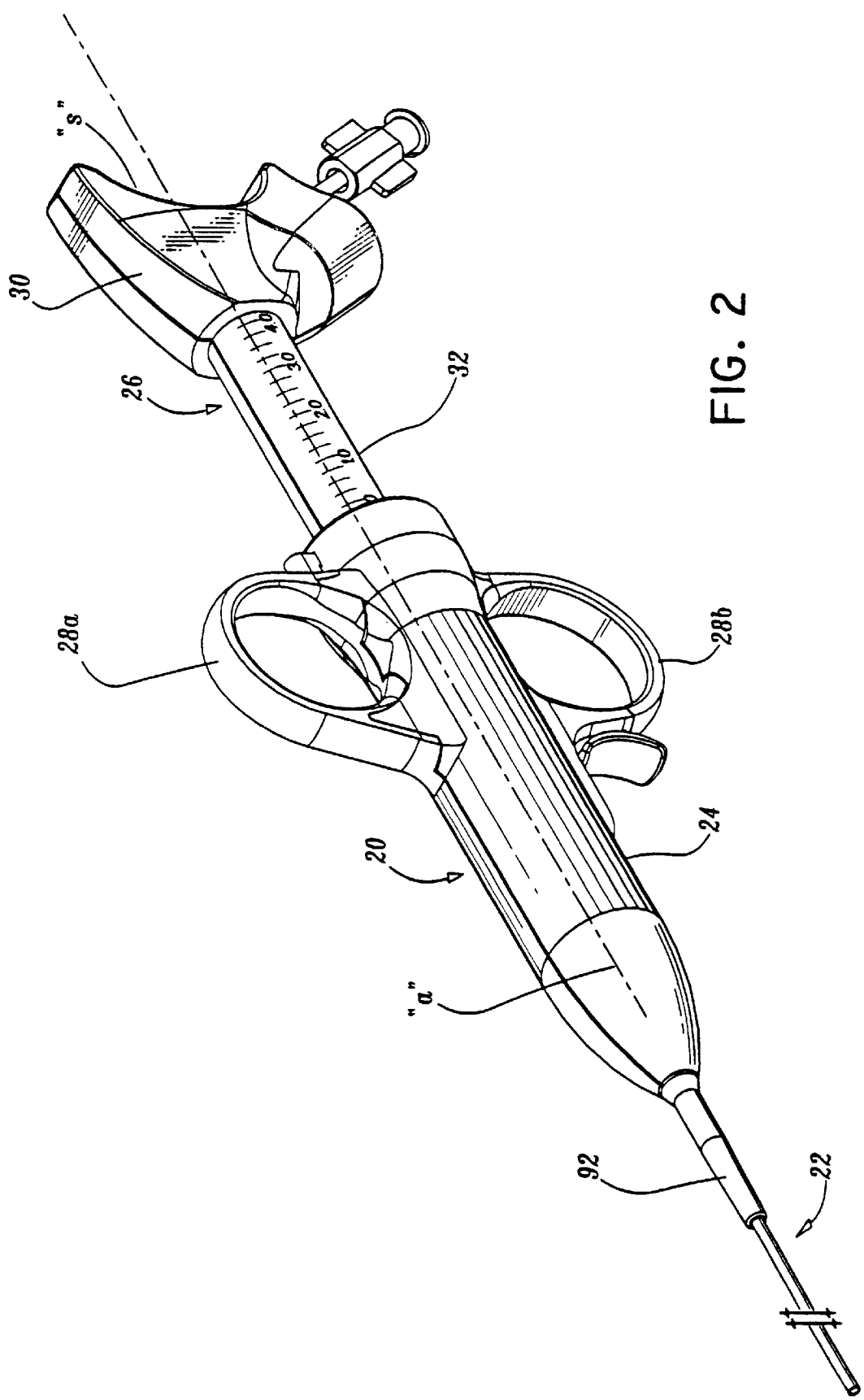
FIG. 2 is a perspective view of the electrosurgical instrument of the apparatus of FIG. 1 illustrating the handle and the elongated portion connected to the handle.
Figure 3:
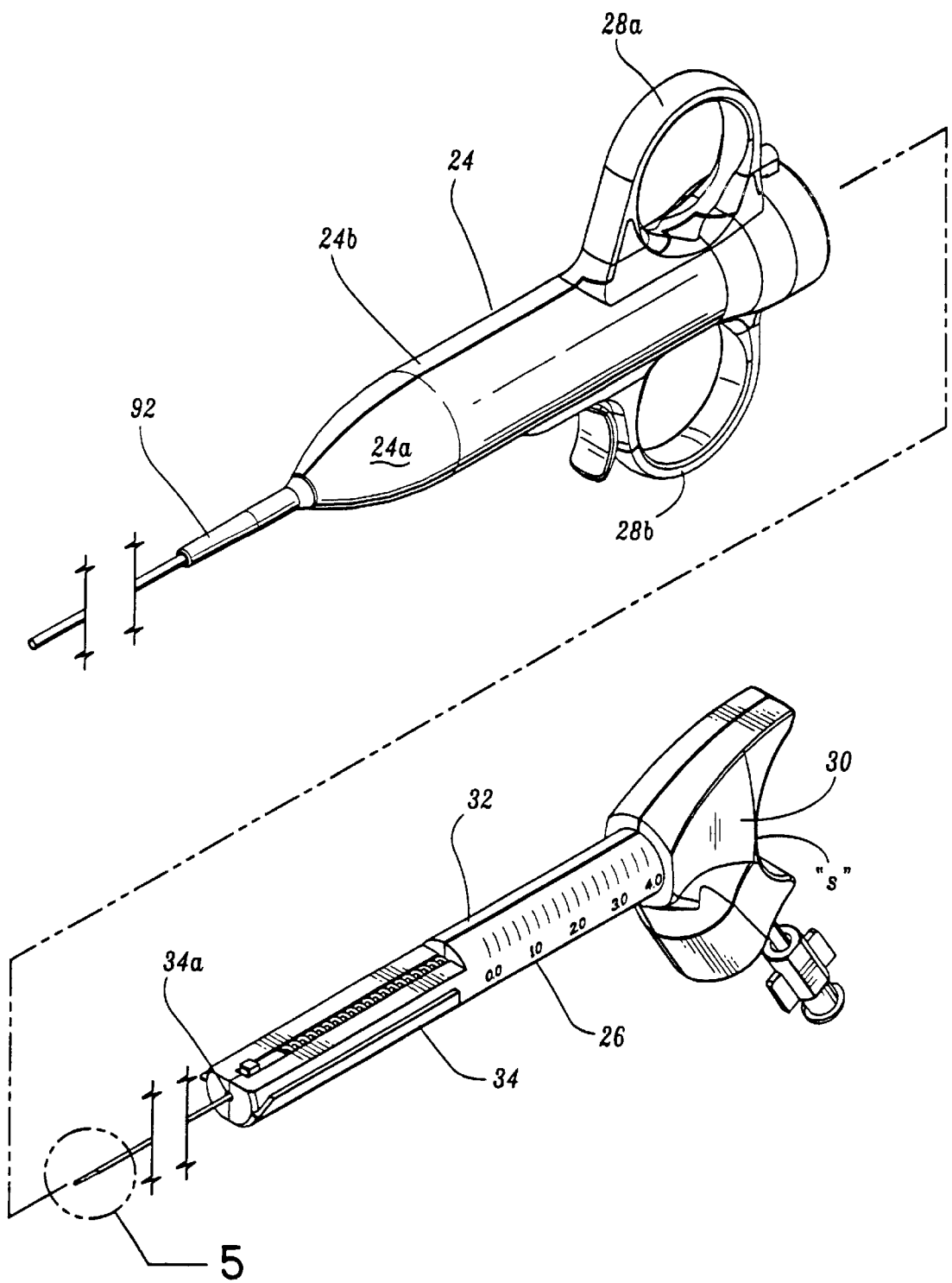
FIG. 3 is a disassembled view of the handle of the electrosurgical instrument illustrating the frame and the actuator mounted to the frame.

Referring now to FIGS. 2–3, electrosurgical instrument 12 of apparatus 10 will be discussed in detail. Instrument 12 includes handle 20 and elongate portion 22 connected to the handle 20 and extending distally therefrom, and defining longitudinal axis "a". Handle 20 includes main frame 24 and electrode actuator 26 which is mounted for movement relative to the frame 24. Frame 24 consists of frame half sections 24a, 24b which are connected to each other along respective peripheral areas with suitable means including adhesives, cements, screws, etc. Frame 24 defines diametrically opposed finger loops 28a, 28b which are advantageously dimensioned to receive the index and middle fingers respectively of the operator.

Electrode actuator 26 includes two sections, namely, manual engaging proximal portion 30 and distal extension 32 connected to the manual portion 30. Manual portion 30 defines an arcuate outer surface area "s" which is contoured to accommodate the palm area of the user's hand. Distal extension 32 is received within a corresponding dimensioned longitudinal bore or channel of main frame 24 and is adapted for reciprocal longitudinal movement therewithin to deploy an electromagnetic probe connected to the electrode actuator 26. Distal extension 32 includes first and second longitudinally extending opposed rails 34 on its outer surface. Rails 34 define distal camming rail surfaces 34a. Electrode actuator 26 is releasably mounted to frame 24 to permit rapid disassembly and subsequent, if desired, insertion and mounting of a different actuator 26 having different energy transmitting capabilities as will be discussed.

The remaining components of handle 20 will be described in detail hereinbelow.

Figure 4:
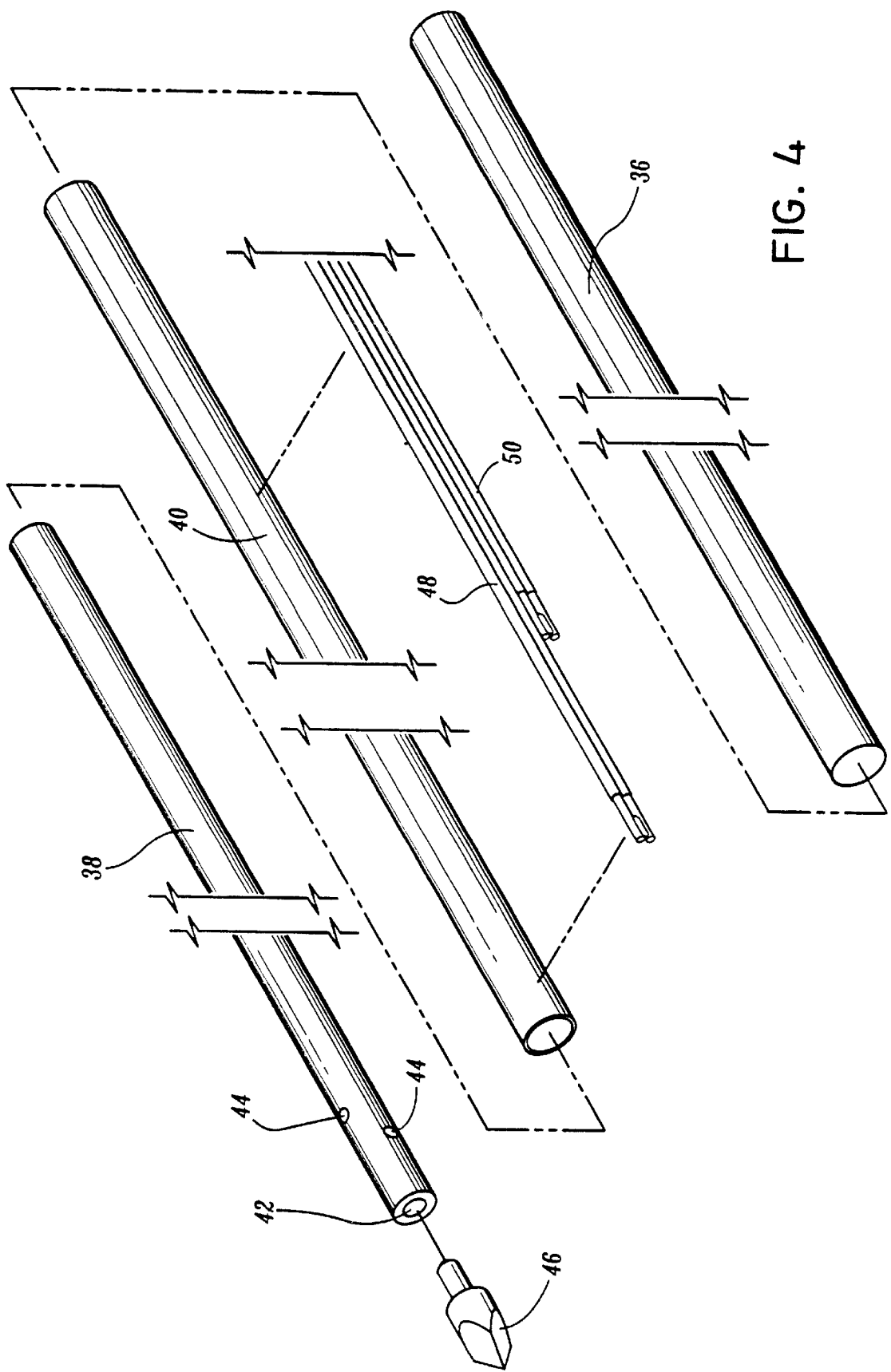
FIG. 4 is a perspective view with parts separated of the elongated portion of the electrosurgical instrument.
Figure 5:
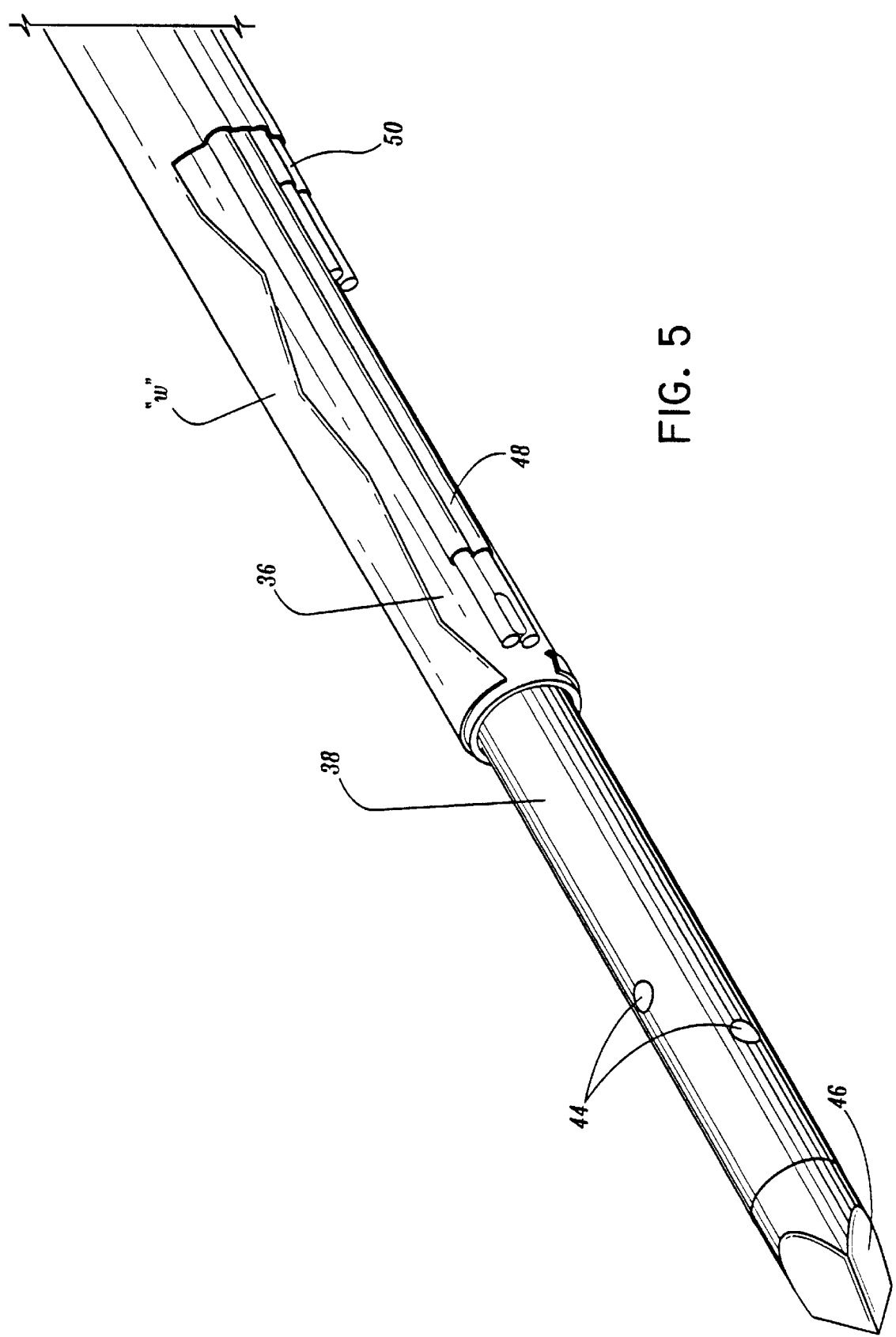
FIG. 5 is an enlarged perspective view of the distal end of the elongated member with a portion cut-away illustrating the electromagnetic probe and the thermocouples associated with the electromagnetic probe.

Referring now to FIGS. 4–5, elongate portion 22 of instrument 12 will be discussed. Elongate portion 22 includes outer sleeve 36 which is preferably flexible and manufactured from a suitable flexible elastomeric or polymeric material. It is envisioned that outer sleeve 36 may be rigid and manufactured, e.g., from stainless steel, titanium or a rigid polymer. An electromagnetic probe 38 is disposed within outer sleeve 36 and is reciprocally movable therewithin. Electromagnetic probe 38 is preferably configured as an RF electrode and has an insulating layer 40 coaxially mounted thereabout. As is conventional, the distal end of electromagnetic probe is uninsulated to transmit the electromagnetic (RF) energy. Electromagnetic probe 38 has an axial channel 42 for passage of the irrigant fluids or, if desired, conductive fluids. A plurality of perforations or openings 44 extend through the outer wall of electromagnetic probe 38 in communication with the axial channel 42 to permit exit of the irrigant into the treatment site. The distal end of electromagnetic probe 38 has a penetrating end member 46 connected thereto which defines a closed pointed end dimensioned to facilitate passage of the probe 38 through tissue. Although shown as a separate component, it is envisioned that penetrating end member 46 may be integrally formed with electromagnetic probe as a single unit.

Elongate portion 22 may further include a pair of thermocouples 48, 50 which extend along the exterior surface of outer sleeve 36. The first thermocouple 48 extends to a position adjacent the distal end of outer sleeve 36 and is intended to measure the temperature of the tissue within the treatment area for monitoring purposes. The second thermocouple 50 extends to a position displaced from the distal end of outer sleeve 36 and is intended to measure the temperature of tissue outside and adjacent the treatment area to ensure that this tissue is not undesirably treated. Shrink wrapping "w" (FIG. 5) is disposed about outer sleeve 36 and thermoc thermocouples 48, 50.

Figure 6:
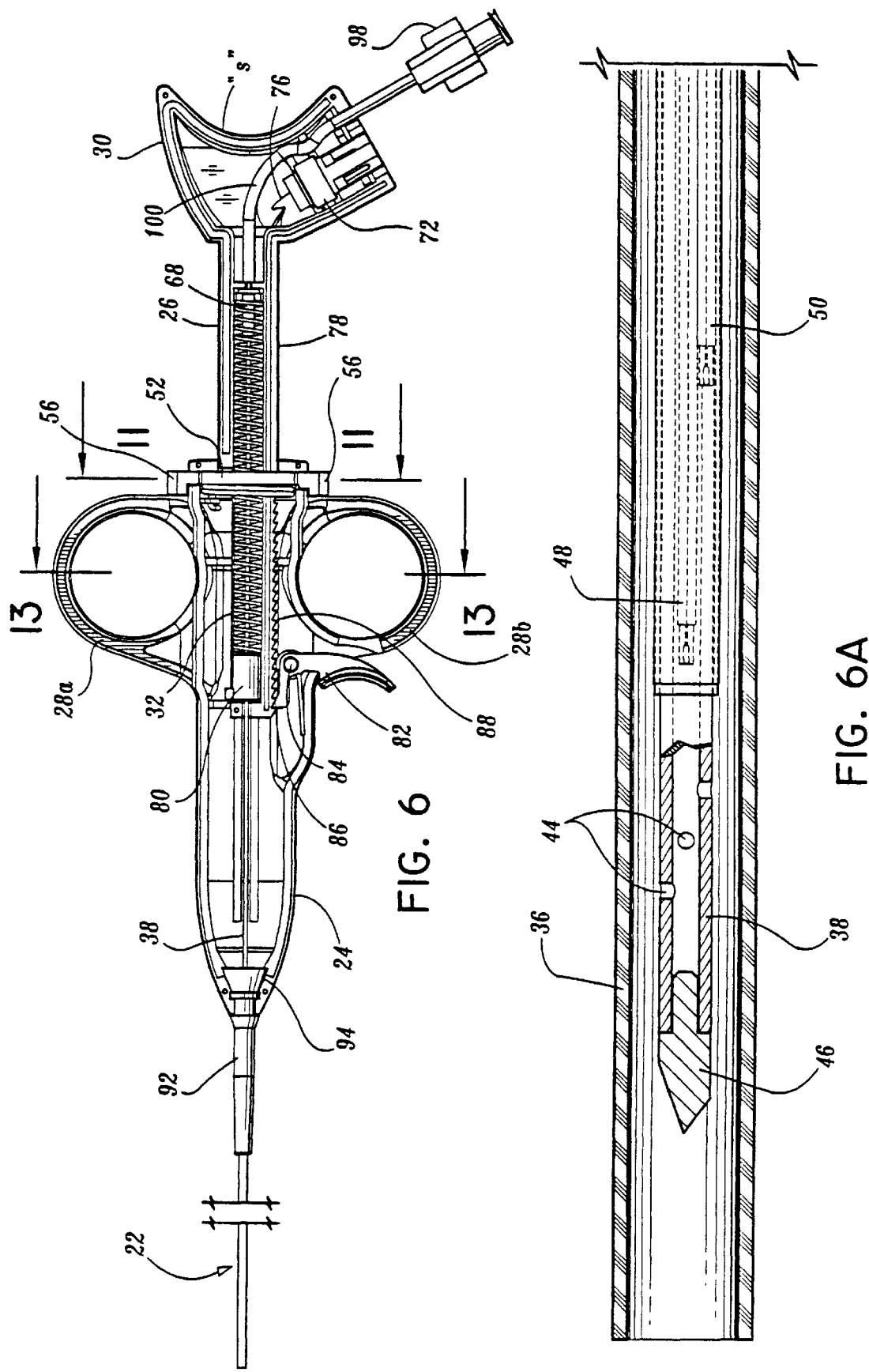
FIG. 6 is a cross-sectional view of the handle of the electrosurgical instrument in an initial unactuated position.
Figure 7:
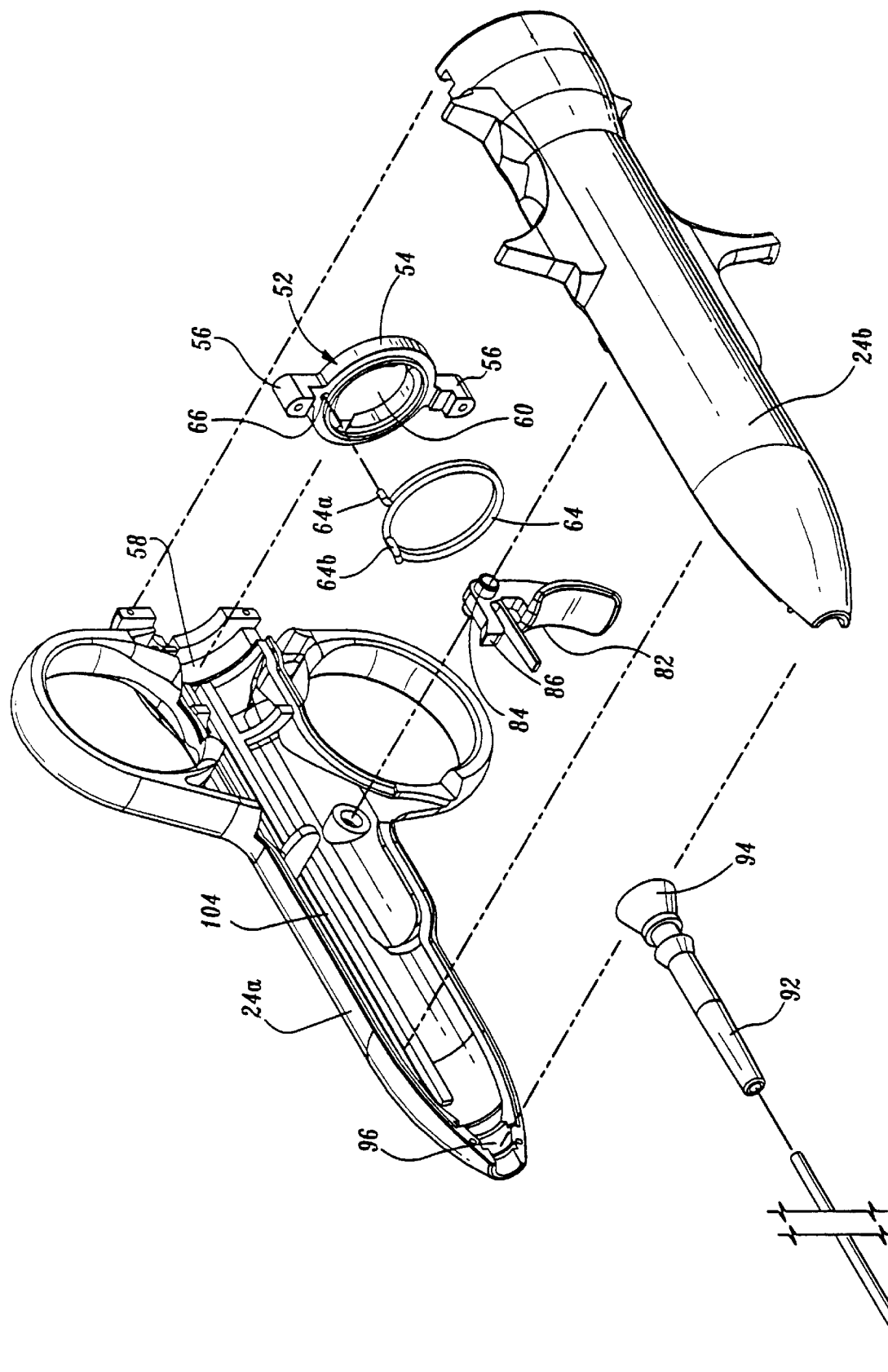
FIG. 7 is a perspective view with parts separated illustrating the components of the frame of the handle.
Figure 8:
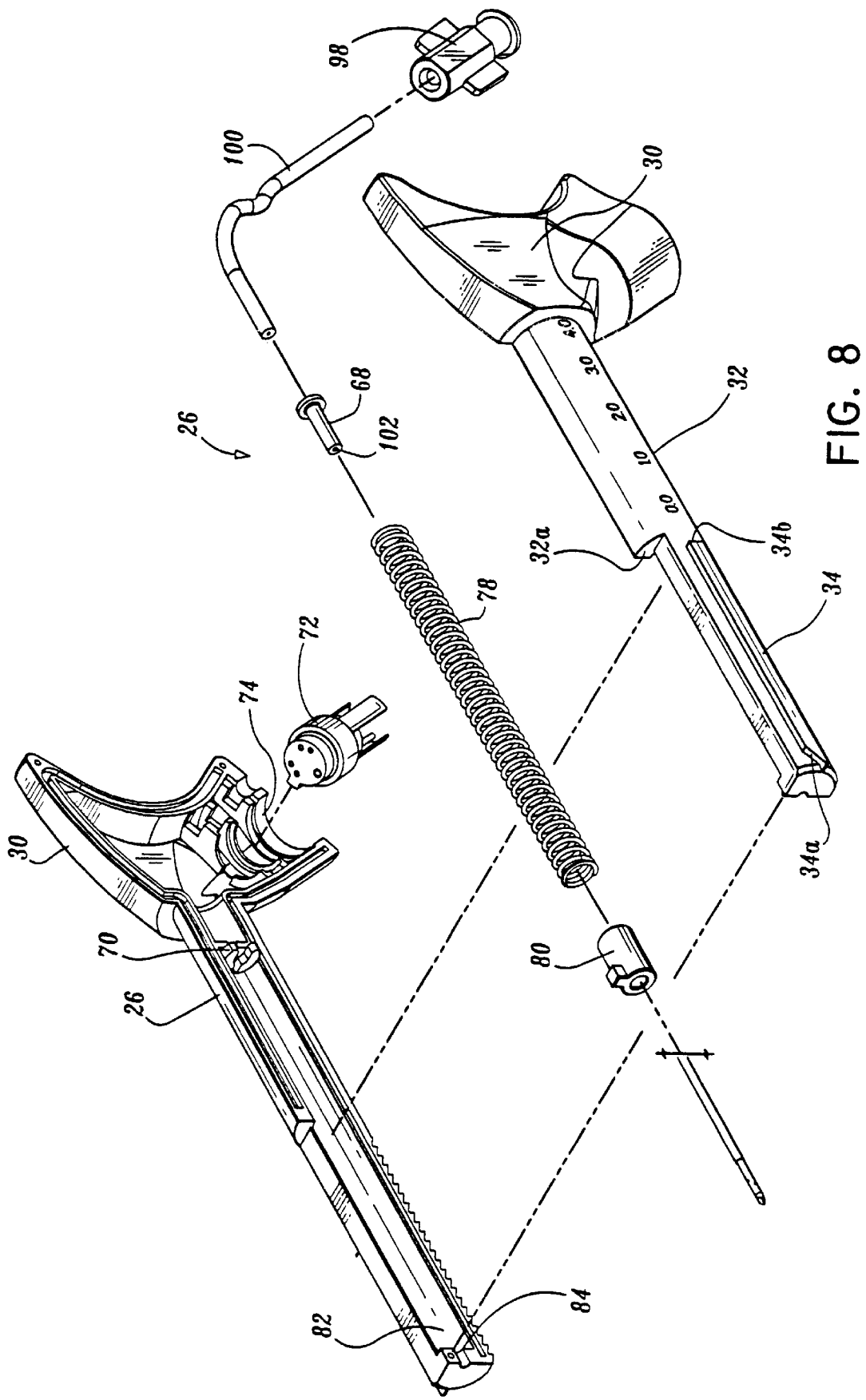
FIG. 8 is a perspective view with parts separated illustrating the components of the actuator of the electrosurgical instrument.
Figure 9:
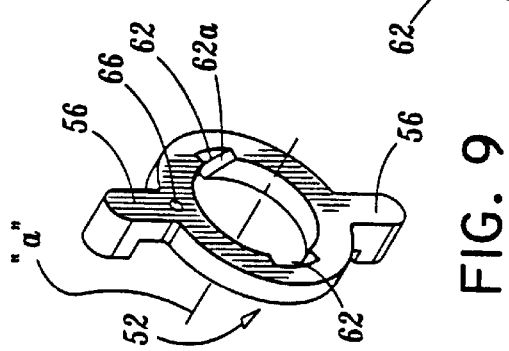
FIGS. 9–10 are views illustrating the assembly member of the electrosurgical instrument.
Figure 10:
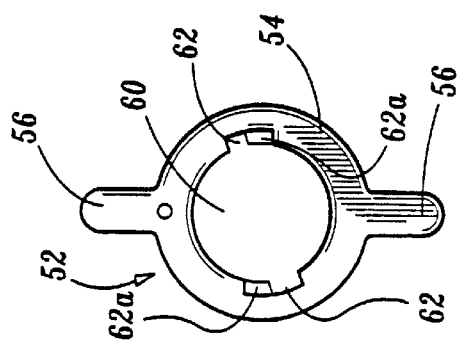

Referring now to FIGS. 6–8, the mechanical connection of elongate portion 22 with handle 20, and the remaining components of the handle 20 will be discussed. Handle 20 includes quick release or assembly member 52 mounted to the proximal end of frame 24. Assembly member 52 is adapted to releasably lock actuator 26 to frame 24, and is movable from a first or engaged position preventing removal of actuator 26 from frame 24 to a second or disengaged position permitting removal of the actuator 26 from the frame 24. As best depicted in FIGS. 9–10, assembly member 52 includes a generally circular main portion 54 and diametrical opposed tabs 56 extending from the main portion 54. Main portion 54 is accommodated within correspondingly dimensioned arcuate grooves 58 formed in each of frame sections 24a, 24b. Grooves 58 are dimensioned to permit main portion 54 to rotate within frame 24 about axis "a". Main portion 54 defines central aperture 60 which is configured to receive distal extension 32 of actuator 26 and permit sliding movement of the distal extension 32 therethrough. As best depicted in FIGS. 9–10, main portion 54 of assembly member 52 further defines a pair of grooves 62 adjacent aperture 60 and arranged in diametrical opposed relation. Grooves 62 are arranged to define slanted or oblique cam surface 62a, i.e., the grooves 62 extend in an oblique relation with respect to a central axis "a" of assembly member 52, the significance of which will be discussed in detail hereinbelow.

Figure 11:
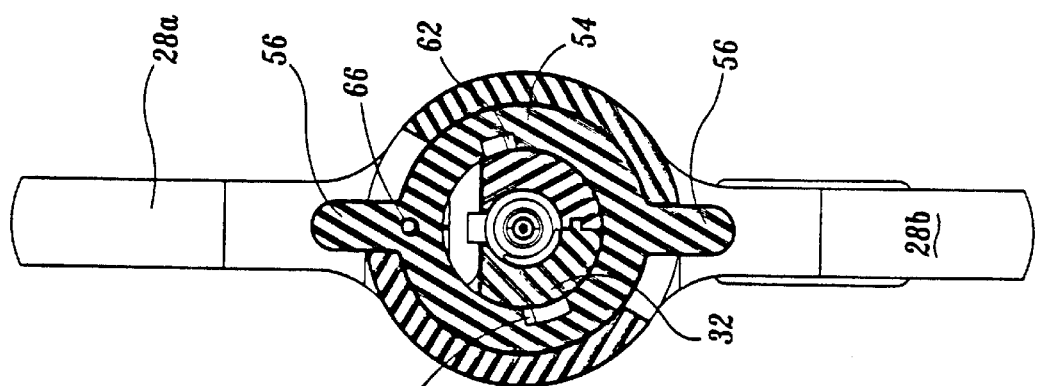
FIG. 11 is a cross-sectional view taken along the lines 11—11 of FIG. 6 illustrating the assembly member in a locked position preventing disassembly of the actuator and the electromagnetic probe.

With reference now to FIGS. 6 and 7, a coil spring 64 is mounted adjacent assembly member 52 and possesses spring end portions 64a, 64b. Spring end portion 64a is received within correspondingly dimensioned aperture 66 of assembly member 52. (See also FIGS. 9–10.) Spring end portion 64b engages corresponding structure 68 of frame 24 to fix the end portion 64b to the frame 24. In this manner, coil spring 64 normally biases assembly member 52 to the first or engaged position which is depicted in FIG. 11.

With reference now to FIGS. 6 and 8, electromagnetic probe 38 extends within frame 24 of handle 20 and is operatively connected to actuator 26. In a preferred arrangement, electromagnetic probe 38 is connected to ferrule 68 by suitable means including adhesives, cements, crimping or the like. Ferrule 68, in turn, is accommodated within ferrule connection tab 70 of actuator 26 and is fixed to the tab 70 by a snap lock fit or a bayonet coupling. Accordingly, reciprocal longitudinal movement of actuator 26 causes corresponding movement of electromagnetic probe 38 between an initial position and an advanced deployed position. Electromagnetic probe 38 is electrically connected to power source 14 through electrical connector 72 which is mounted within a corresponding recess 74 of actuator 26. A feed line 76 (FIG. 6) extends from electrical connector 56 to electromagnetic probe 38 to electrically connect the two components.

In FIGS. 6 and 6A, actuator 26 is depicted in the initial position where electromagnetic probe 38 is contained within outer sleeve 36 as depicted in FIG. 6A. Actuator 26 is normally biased to the initial position by compression or coiled spring 78. More specifically, compression spring 78 engages at its distal end spring mount 80 which is positioned within recess 82 (FIG. 8) and against bearing surface 84 of actuator 26. At its proximal end, compression spring 78 engages ferrule 68 to thereby bias ferrule 68 and, thus, electromagnetic probe 38 and actuator 26, proximally to the initial position depicted in FIG. 6.

With reference to FIG. 7, taken now in conjunction with FIG. 6, a release trigger 82 is pivotally mounted to frame 24 about pivot pin 84. Release trigger 82 includes a pawl 86. Similarly, actuator 26 has a ratchet portion 88 actuator 26. (See also FIG. 8.) Pawl 86 of release trigger 82 engages the teeth of ratchet portion 88 to selectively releasably lock actuator 26 at predetermined positions between the initial position and the deployed position thereof while preventing return motion of the actuator 26, to thereby enable the operator to selectively control the degree of extension of electromagnetic probe 38 beyond outer sleeve 36. The pawl and ratchet arrangement also provides a perceptible audio indicator to the user indicating the degree of advancement of the electromagnetic probe.

Release trigger 82 is adapted to pivot about pivot pin 84 from the engaged position of FIG. 6 where pawl 86 is in locking engagement with ratchet portion 88 to lock actuator 26 and electromagnetic probe 38 at a desired extended position, and a disengaged position where pawl 86 is in disengaged relation with the ratchet portion 88 thereby permitting actuator 26 to return to the initial position under the influence of compression spring 78. A leaf spring 90 normally biases release trigger 82 to its engaged position.

With continued reference to FIGS. 6 and 7, handle 20 also includes connector sleeve 92 for connecting outer sleeve 36 to frame 24. Connector sleeve 92 includes proximal flange 94 which is received within a corresponding dimensioned recess 96 of frame 24 to connect the two components. With reference to FIGS. 6 and 8, handle 20 further includes luer connector 98 which conveys through tube 100 extending through actuator 26 the irrigant or conductive fluid. Tube 100 is in fluid communication with an internal bore 102 of ferrule 68 (FIG. 8). Internal bore 102 is in fluid communication with axial channel 42 of electromagnetic probe 38.

Figure 12:
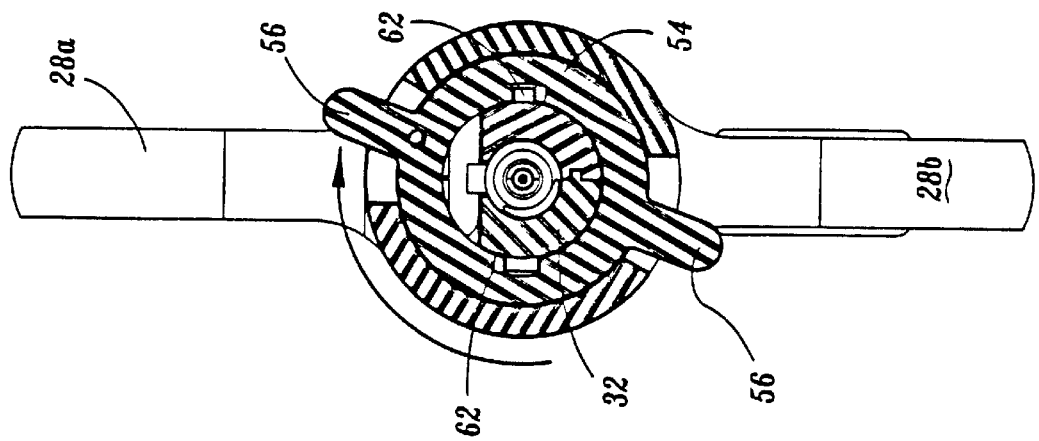
FIG. 12 is a view similar to the view of FIG. 11 illustrating the assembly member in an unlocked position permitting disassembly of the actuator and electromagnetic probe.

The assembly of instrument 12 will now be discussed. To assemble actuator 26 within frame 24, distal extension 32 of the actuator 26 is inserted in the proximal end of the frame 24 with distal cam surfaces 34a of external rails 34 on the exterior surface of actuator 26 being received within grooves 62 of quick assembly member 52 (FIG. 10). Actuator 26 is advanced within frame 24 whereby during advancement cam surfaces 34a ride along inclined cam surfaces 62a defined by grooves 62 to cause assembly member 52 to rotate in the direction depicted in FIG. 12. Once rails 34 of actuator 26 have cleared the grooves 62 of assembly member 52, the assembly member 52 rotates under the influence of spring 64 to its initial position depicted in FIG. 11. In this position, actuator 26 is prevented from moving in the proximal direction, due to engagement of the proximal end faces 34b of rails 34 (FIG. 8) with the distal end surface 52a of assembly member 52, i.e., in the assembled position, rails 34 of actuator 26 are not aligned with grooves 62 of assembly member 52 thereby preventing movement of the actuator 26 in the proximal direction thus preventing disassembly of the actuator 26 from the frame 24. To remove actuator 26 from frame 24, assembly member 52 is rotated in the direction of the directional arrow of FIG. 12 to align grooves 62 of assembly member 52 with rails 34 of actuator 26 to permit the actuator 26 to be moved in the frame 24.

Figure 13:
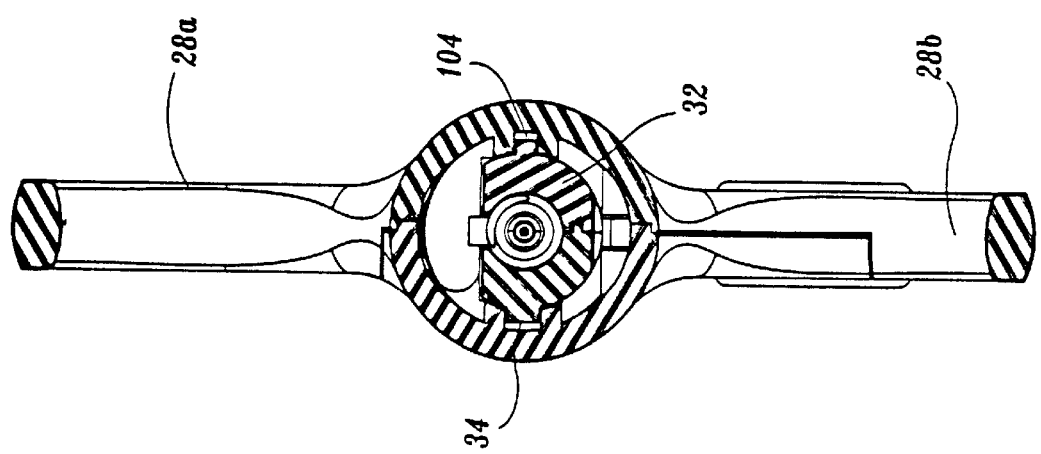
FIG. 13 is a cross-sectional view taken along the lines 13—13 of FIG. 6.

FIG. 13 is a cross-sectional view taken along the lines 13—13 of FIG. 6. As depicted in FIG. 13, in the assembled condition, rails 34 of actuator 26 are accommodated within longitudinal recesses 104 formed in frame half sections 24a, 24b (FIG. 7) and are guided by and confined within the recesses during advancement of the actuator 26 thereby preventing the actuator 26 from rotating within the frame 24.

Referring now to FIG. 14, electrosurgical instrument 12 is shown positioned within a conventional cystoscope 200 for thermal treatment of prostrate "p" to alleviate the symptoms of BPH. One conventional cystoscope 200 with which the apparatus of the present disclosure can be utilized is the ACN Flexible CystoNephroscope manufactured by Circon ACMI of Stamford, Conn. Cystoscope 200 includes handle 202 and a flexible elongated portion 204 connected to the handle 202 and extending distally therefrom. Cystoscope 200 incorporates an optical apparatus to permit viewing of the tissue to be treated. As depicted in FIG. 15, the optical system preferably consists of flexible fiber optic bundles (identified by reference numeral 206) which are accommodated within a longitudinal bore extending through the elongated portion 204 of the scope 200. The fiber optic bundles 206 extend to eyepiece 208 where the surgeon can view the image transmitted by the optical system.

Cystoscope 200 also includes an illumination system which provides illuminating light to the targeted tissue area. The illumination system includes a plurality of optical fibers 210 which are accommodated within a plurality of longitudinal channels (two are shown) of elongated portion 204 and extend within handle 202 where they terminate at illumination coupler 212. Illumination coupler 212 is connectable to a conventional light source as is known in the art. Cystoscope 200 further includes a working channel 214 (FIG. 16) extending through flexible elongated portion 204 and terminating at channel port 216 of handle 202. Working channel 214 is adapted to receive various surgical inst 216 (e.g., electrosurgical instrument 12) to permit the performance of surgical procedures at the distal end of the cystoscope 200. Cystoscope 200 is preferably a 5 mm scope. Cystoscope 200 is further characterized by being a steerable scope, i.e., the distal end of the scope may be manipulated to a variety of different angles and orientation, via handle or control knob mounted on the proximal end of the scope.

Operation

The use of apparatus 10 with cystoscope 200 in conjunction with the thermal treatment of prostatic tissue will now be discussed. Cystoscope 200 is inserted through urethral passage "u" of the patient and advanced within the passage until the distal end of the scope is adjacent prostate gland "p". Thereafter, elongate portion 22 of instrument 12 is inserted into working channel 214 of cystoscope 200 and advanced into the working channel 214 until handle 20 of the instrument 12 contacts channel port 216 of scope handle 202. As an alternative method of insertion, instrument 12 may be positioned within cystoscope 200 prior to insertion within the urethral passage "u" and the entire assembly may be then advanced within the urethral passage. It is envisioned that handle 20 of instrument 12 may incorporate a locking mechanism to lockingly engage channel port 216 of handle 202 of the cystoscope 200.

Figure 17:
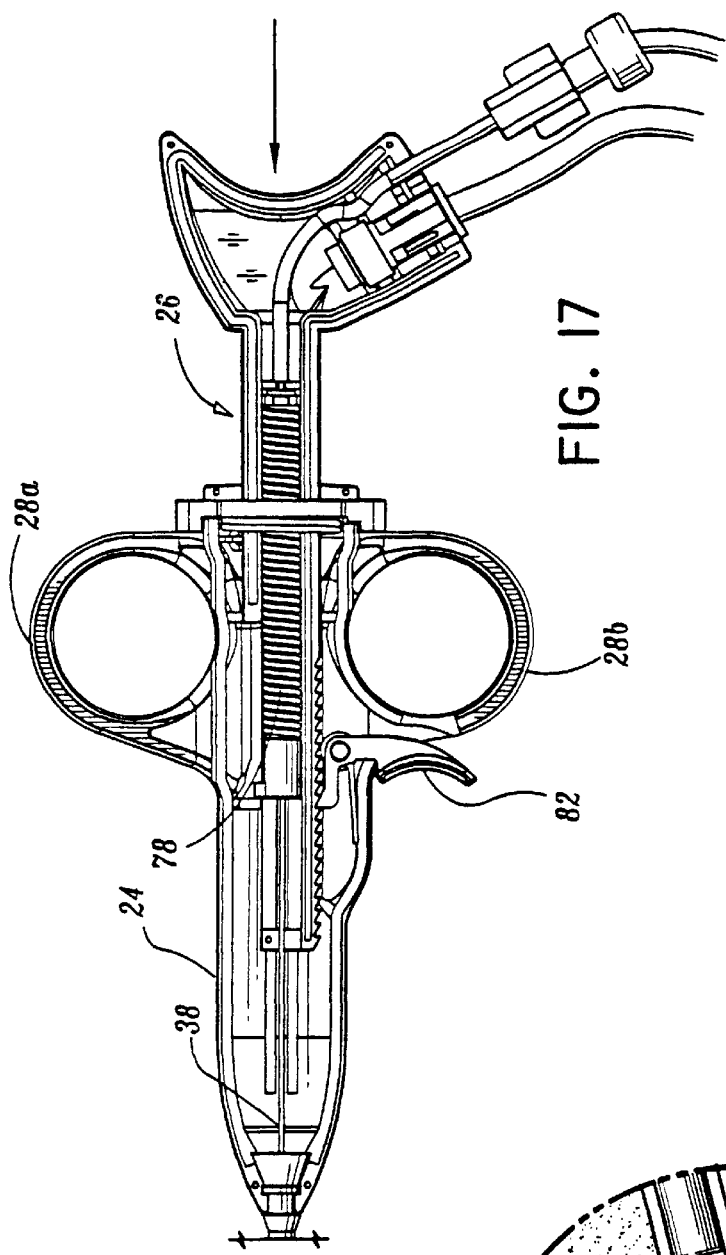
FIG. 17 is a cross-sectional view of the handle of the electrosurgical instrument illustrating actuation of the actuator to deploy the electromagnetic probe.
Figure 18:
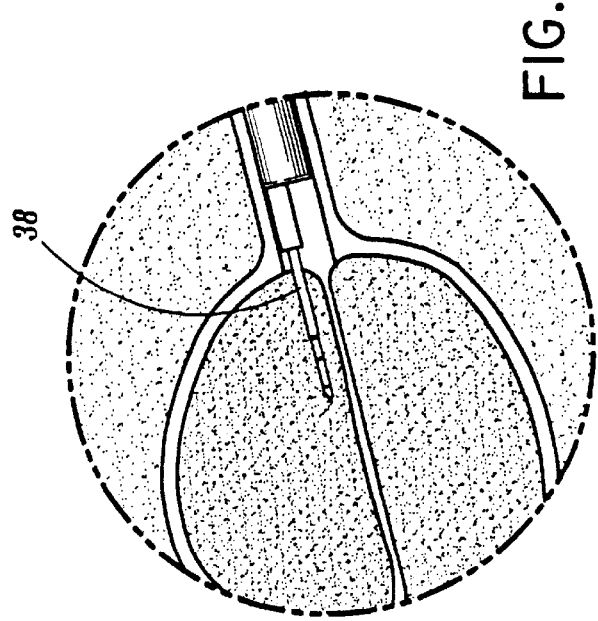
FIG. 18 is a view illustrating penetration of the electromagnetic probe within the prostrate corresponding to the position of the actuator in FIG. 17.

With reference now to FIGS. 17–18, electrode actuator 26 is distally advanced to move or deploy electromagnetic probe 38 from outer sleeve 36 of the instrument and the distal end face of cystoscope 200. The degree of deployment of electromagnetic probe 38 is monitored both audibly by virtue of the ratchet and associated pawl mechanism and visually by virtue of the gradient markings "m" on the external surface of the actuator 26 (FIG. 2). In addition, pawl 86 of release trigger 82 releasably locks or secures the actuator 26 and electromagnetic probe 38 at any desired predetermined intermediate position. Advancement of the electromagnetic probe 38 causes the distal end portion of the probe to enter the prostate. The location of the probe end portion may be visually monitored with the optical system of the cystoscope 200.

The apparatus is then energized to thermally treat (e.g., ablate, vaporize or cauterize) the desired prosthetic tissue with RF energy. As a result of this treatment, the prosthetic tissue BPH necroses and dies, thus, relieving pressure off the urethral wall and alleviating the symptoms of BPH. During treatment, the depth of penetration of penetrating end portions of electromagnetic probe 38 may be selectively adjusted by movement of actuator 26 to permit specific regions of the prosthetic tissue "p" to be targeted for thermal treatment thus providing heating pattern flexibility and control. During treatment, insulating layer 40 of electromagnetic probe 38 preferably contacts the urethral wall "u" to prevent damage to the wall. During treatment, an irrigant agent may be dispensed through apertures 44 of electromagnetic probe 38 to flush and cool the area adjacent the probe end portion as depicted in FIG. 19. Alternatively, a conductive agent may be dispensed through the apertures 44 to facilitate heat transfer to enhance the ablation process.

Figure 21:
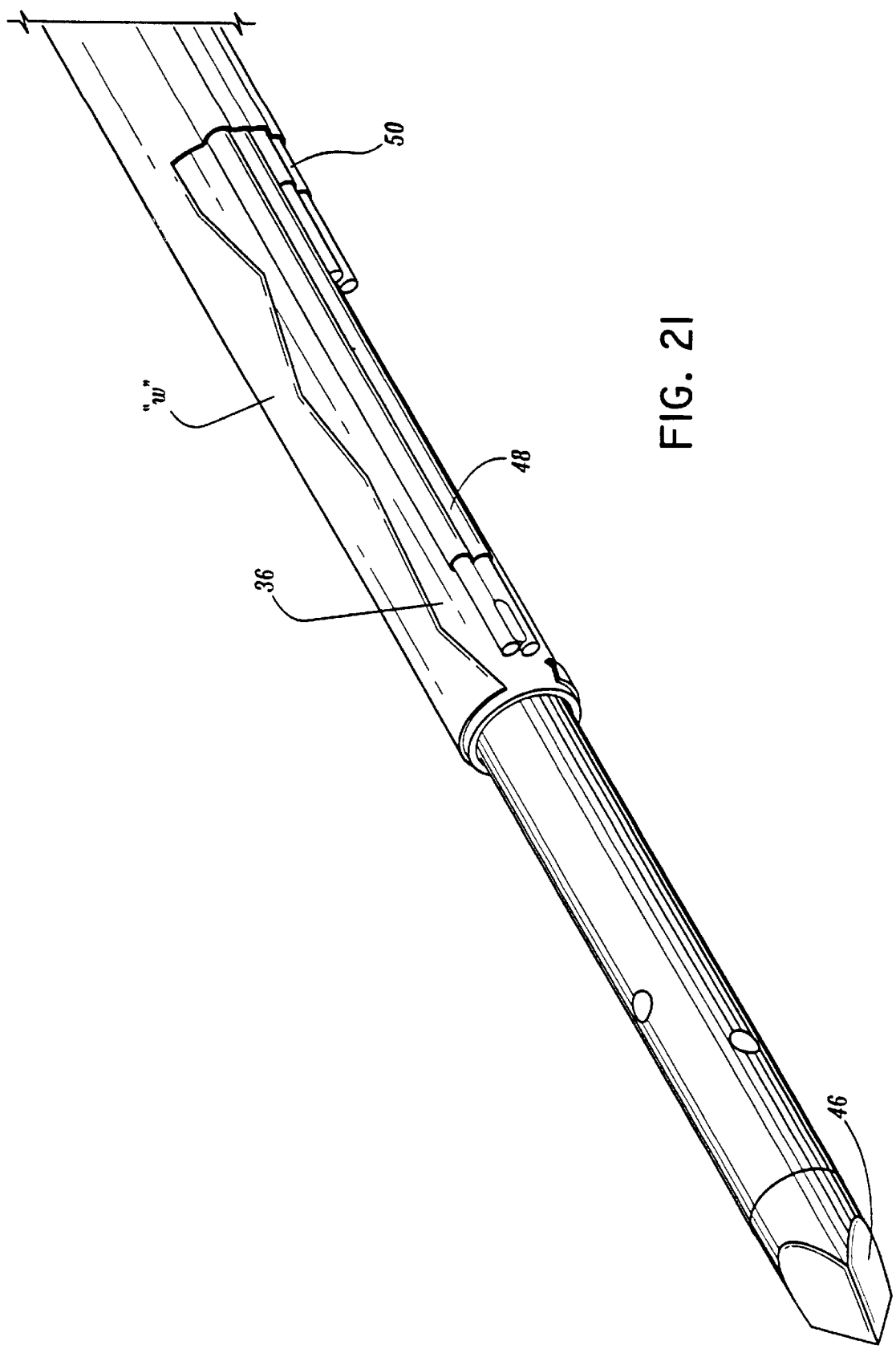
FIG. 21 is a perspective view of an alternate actuator and electromagnetic probe connectable to the electrosurgical instrument.

Upon completion of the treatment, the apparatus is de-energized and the cystoscope 200 and apparatus are removed from the urethral passage "u". Thereafter, release trigger 82 is depressed to release the ratchet and pawl thereby permitting actuator 26 to return to its initial position under the influence of compression spring 78 as depicted in FIG. 20. Actuator 26 is then removed by rotating assembly member 52 to the position depicted in FIG. 12 to align the grooves 62 of the assembly member 52 with rails 34 of actuator 26 thereby permitting removal of the electrode actuator. If desired, a second actuator 26 and associated electrode unit having different energy transmitting properties (e.g., a greater portion of electrode 38 uninsulated) such as the unit depicted in FIG. 21 (compare FIG. 5) may be mounted to frame 24 to continue treatment.

Figures 22, 23:
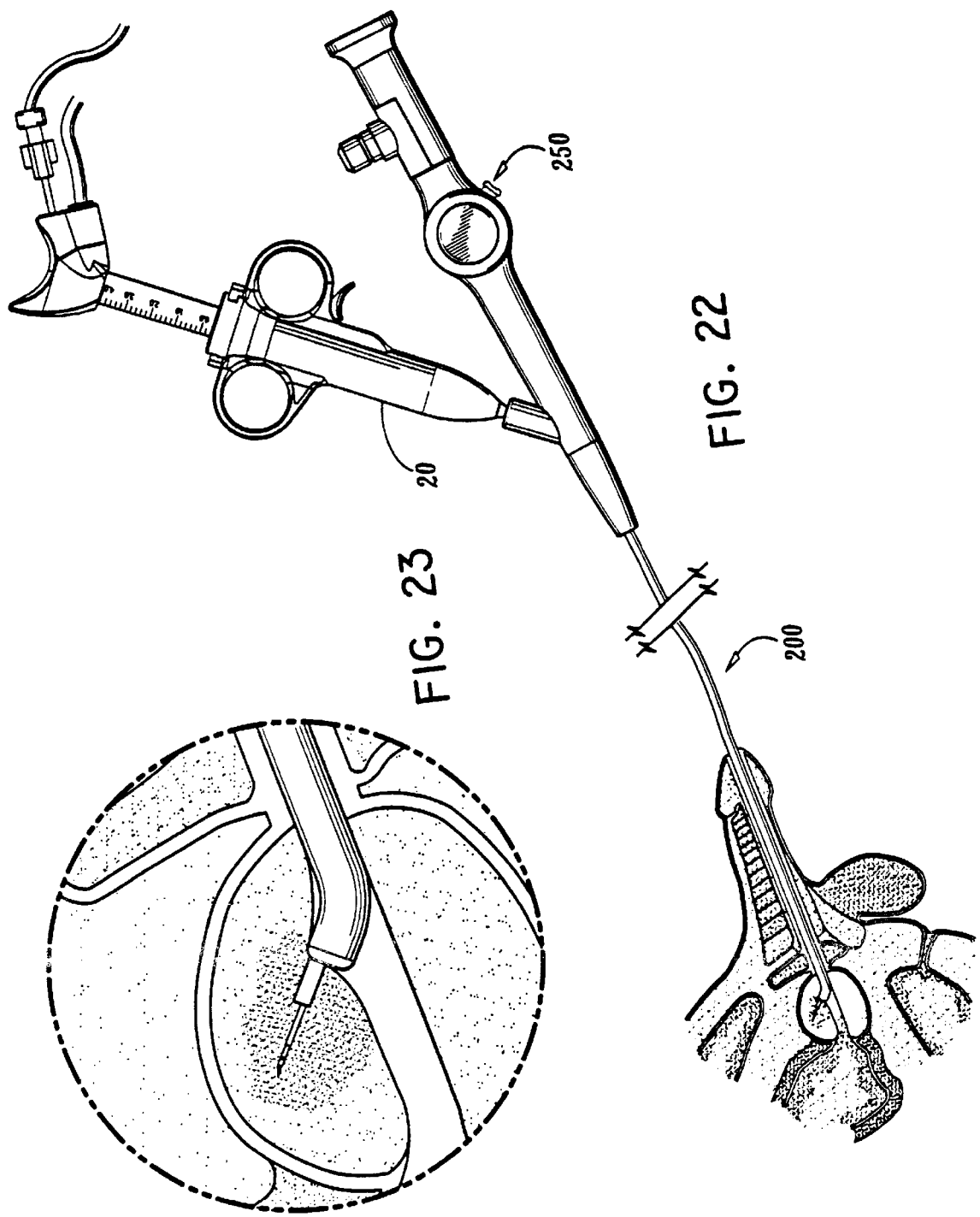
FIG. 22 is a view illustrating a steerable cystoscope inserted within the urethral passage and having the electrosurgical instrument mounted therein.
FIG. 23 is an enlarged isolated view illustrating the distal end of the cystoscope deflected at a desired angular orientation with the electromagnetic probe deployed.

The assembly mechanism enables the operator to select a desired actuator and associated electrode unit to achieve a desired operative parameter and quickly and efficiently mount the actuator to the apparatus. It is envisioned that the apparatus may be sold as a kit with several different actuator and electrode units having different energy transmitting capabilities, for example, including the units depicted in FIG. 5 and FIG. 21. In addition, subsequent to treatment, the actuator may be quickly removed for disposal or sterilization if desired. Moreover, in that only the actuator and electrode unit are subjected to the operative site, only this unit would require sterilization thereby minimizing maintenance costs of the apparatus and enhancing the life thereof With reference to FIGS. 22–23, in an alternate arrangement, apparatus 10 may be used with a cystoscope 200 having steerable capabilities whereby the distal end of the scope 200 may be manipulated at a variety of different angles and orientations via a handle or control lever 250 mounted adjacent the proximal end of the scope. With the steerable cystoscope, the distal end is manipulated to a desired angle and the electrode 38 is thereafter deployed at the desired angle to penetrate the prostate. One suitable steerable cystoscope is disclosed in U.S. Pat. No. 5,704,898, the contents of which are incorporated herein by reference.

Although certain embodiments and examples have been used to illustrate and describe the present invention, it is intended that the scope of the invention not be limited to the specific embodiments set forth herein.

What is claimed is:

1. An apparatus for thermal treatment of tissue, which comprises:
an outer member including a frame dimensioned for engagement with the hand of a surgeon and an elongated portion connected to the frame and extending distally therefrom, the elongated portion defining a longitudinal axis and having an axial opening;
an electromagnetic probe assembly releasably mounted to the outer member, the electromagnetic probe assembly including a handle and an electromagnetic probe connected to the handle, the electromagnetic probe at least partially positionable within the axial opening of the elongated portion and adapted for reciprocal longitudinal movement therewithin between a non-deployed position and a deployed position; and
a manually operable release member for releasably mounting the electromagnetic probe assembly to the outer member, the release member dimensioned and positioned for manual manipulation to move between a first position engaging the electromagnetic probe assembly and preventing release thereof from the outer member, and a second position releasing the electromagnetic probe assembly to thereby facilitate assembly and disassembly of the electromagnetic probe assembly with respect to the outer member.

2. The apparatus according to claim 1 wherein the release member is mounted to the frame of the outer member.

3. The apparatus according to claim 2 wherein the release member is rotatable about the longitudinal axis to move between the first and second positions thereof.

4. The apparatus according to claim 3 wherein the release member defines a central opening for reception of a portion of the handle of the electromagnetic probe assembly, the portion of the handle dimensioned for reciprocal longitudinal movement through the opening.

5. The apparatus according to claim 4 wherein the handle of the electromagnetic probe assembly includes a handle extension, the handle extension received within the central opening of the release member.

6. The apparatus according to claim 5 wherein the release member is normally biased to the first position thereof.

7. The apparatus according to claim 6 wherein the release member defines an inner cam surface adjacent the opening and wherein the handle extension of the handle defines a corresponding outer cam surface, the outer cam surface cooperating with the inner cam surface upon advancement of the handle extension within the release member to move the release member to the second position thereof.

8. The apparatus according to claim 7 wherein the handle extension defines an outer rail, the outer rail having the outer cam surface at a distal end thereof and defining an abutment surface at a proximal end thereof, the abutment surface dimensioned and configured to engage the release member to prevent removal of the electromagnetic probe assembly from the outer member when the release member is in the first position thereof and the electromagnetic probe is assembled with respect to the outer member.

9. The apparatus according to claim 8 wherein the handle extension includes first and second diametrically opposed outer rails and wherein the release member includes first and second inner cam surfaces.

10. The apparatus according to claim 8 wherein the frame of the outer member includes at least one longitudinal recess dimensioned for reception of the one outer rail to prevent rotational movement of the electromagnetic probe assembly relative to the outer member.

11. The apparatus according to claim 1 including a ratchet and associated pawl mechanism for permitting controlled incremental movement of the electromagnetic probe assembly toward the deployed position while preventing movement of the electromagnetic probe assembly toward its non-deployed position.

12. The apparatus according to claim 11 including a manually engageable release trigger depending from the frame, the release trigger movable to disengage the ratchet and associated pawl mechanism thereby permitting movement of the electromagnetic probe toward the non-deployed position.

13. The apparatus according to claim 12 wherein the electromagnetic probe is normally biased to the non-deployed position.

14. The apparatus according to claim 1 wherein the electromagnetic probe includes a radio frequency electrode.

15. The apparatus according to claim 14 wherein the electromagnetic probe defines an axial channel for passage of fluids, and at least one opening extending through an outer wall of the probe in fluid communication with the axial channel to permit exit of the fluids therefrom.

16. The apparatus according to claim 15 including a source of fluid communication with the axial channel of the electromagnetic probe.

17. The apparatus according to claim 16 wherein the source of fluid includes one of an irrigant fluid or a conductive fluid.

18. The apparatus according to claim 14 including a second electromagnetic probe assembly, the second electromagnetic probe assembly including a radio frequency electrode having different thermal energy transmitting characteristics relative to the first-mentioned radio-frequency electrode of the first-mentioned electromagnetic probe assembly.

* * * * *